United States Patent
Brahm

(10) Patent No.: US 10,314,715 B2
(45) Date of Patent: Jun. 11, 2019

(54) BIOLOGIC BALLOON AND METHOD OF USE

(71) Applicant: Timothy R. Brahm, Germantown, TN (US)

(72) Inventor: Timothy R. Brahm, Germantown, TN (US)

(73) Assignee: Brahm Holdings, LLC, Germantown, TN (US)

( * ) Notice: Subject to any disclaimer, the term of this patent is extended or adjusted under 35 U.S.C. 154(b) by 330 days.

(21) Appl. No.: 15/250,073

(22) Filed: Aug. 29, 2016

(65) Prior Publication Data

US 2016/0361175 A1 Dec. 15, 2016

Related U.S. Application Data

(63) Continuation of application No. 14/185,362, filed on Feb. 20, 2014, now Pat. No. 9,427,273.

(60) Provisional application No. 61/766,720, filed on Feb. 20, 2013.

(51) Int. Cl.

| | | |
|---|---|---|
| *A61B 17/88* | (2006.01) | |
| *A61F 2/44* | (2006.01) | |
| *A61B 17/70* | (2006.01) | |
| *A61B 17/56* | (2006.01) | |
| *A61L 27/36* | (2006.01) | |
| *A61F 2/46* | (2006.01) | |
| *A61B 17/32* | (2006.01) | |

(52) U.S. Cl.
CPC .............. *A61F 2/441* (2013.01); *A61B 17/56* (2013.01); *A61B 17/70* (2013.01); *A61B 17/7079* (2013.01); *A61B 17/8855* (2013.01); *A61F 2/4601* (2013.01); *A61L 27/3604* (2013.01); *A61L 27/3608* (2013.01); *A61B 2017/320048* (2013.01); *A61B 2017/564* (2013.01); *A61F 2310/00359* (2013.01); *A61F 2310/00365* (2013.01); *A61L 2430/38* (2013.01)

(58) Field of Classification Search
CPC ..... A61B 17/56; A61B 17/70; A61B 17/7079; A61B 17/8855; A61B 2017/320048; A61B 2017/564; A61L 27/3604; A61L 27/3608

See application file for complete search history.

(56) References Cited

U.S. PATENT DOCUMENTS

| | | | | |
|---|---|---|---|---|
| 4,239,492 | A * | 12/1980 | Holman | A61L 27/3604 8/94.11 |
| 4,801,299 | A | 1/1989 | Brendel et al. | |
| 5,131,908 | A | 7/1992 | Dardik et al. | |
| 5,827,289 | A * | 10/1998 | Reiley | A61B 10/025 606/86 R |
| 6,852,095 | B1 * | 2/2005 | Ray | A61B 17/7097 604/93.01 |
| 7,294,144 | B1 * | 11/2007 | Schneider | A61F 2/06 424/423 |
| 8,105,634 | B2 * | 1/2012 | Liu | A61K 9/0024 424/583 |
| 9,427,273 | B2 * | 8/2016 | Brahm | A61B 17/7079 |

(Continued)

FOREIGN PATENT DOCUMENTS

WO WO 2011/091005 7/2011

*Primary Examiner* — Eric S Gibson
(74) *Attorney, Agent, or Firm* — Brinks Gilson & Lione

(57) ABSTRACT

A surgical balloon composed of an aseptically recovered umbilical cord vessel is provided. Methods of preparing a balloon and methods of using the same are also provided.

4 Claims, 1 Drawing Sheet

(56) References Cited

U.S. PATENT DOCUMENTS

2009/0270964 A1   10/2009  Huetter et al.
2014/0236161 A1*  8/2014   Brahm ............... A61B 17/7079
                                                606/93
2016/0361175 A1*  12/2016  Brahm ............... A61B 17/7079

* cited by examiner

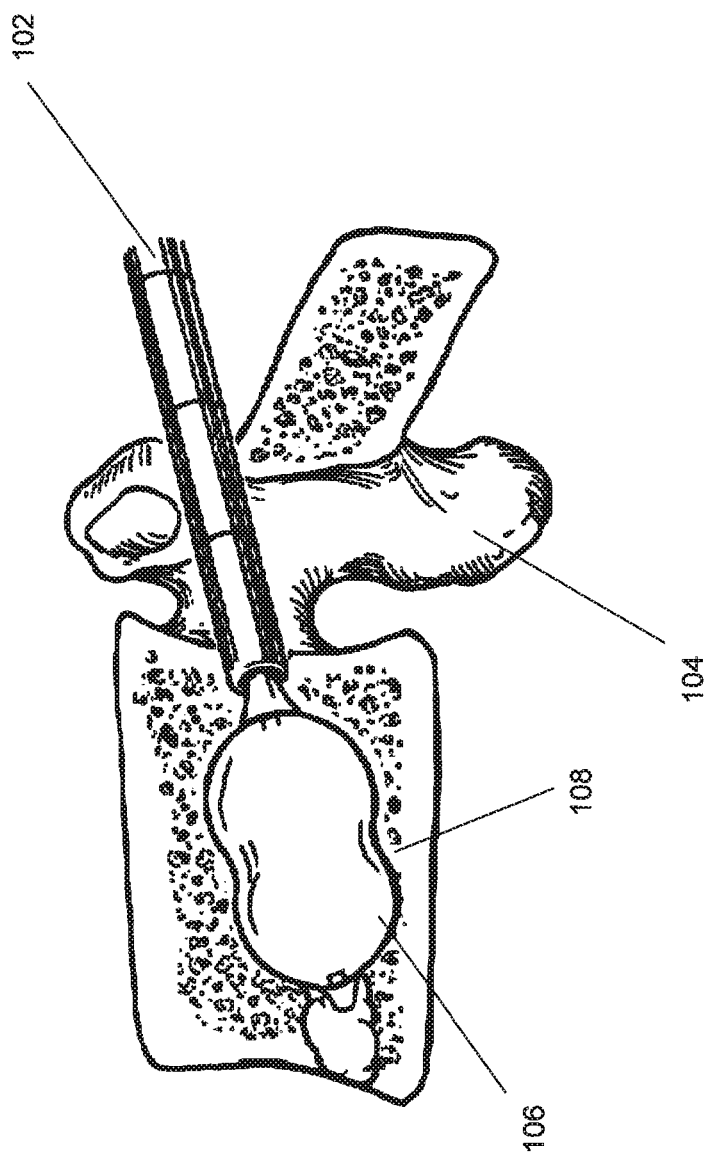

BIOLOGIC BALLOON AND METHOD OF USE

CROSS-REFERENCE TO RELATED APPLICATIONS

This application is a continuation of U.S. application Ser. No. 14/185,362, filed Feb. 20, 2014, which claims priority to U.S. Provisional Application No. 61/766,720 filed Feb. 20, 2013, the contents of which is incorporated by reference in its entirety.

FIELD OF THE INVENTION

The present invention is directed to a surgical balloon composed of an aseptically recovered umbilical cord vessel, methods of preparing such a balloon, and methods of using the same.

BACKGROUND OF THE INVENTION

A vertebral compression fracture occurs when the bones of the spine become broken due to trauma. Methods to strengthen vertebral bodies have evolved with significant clinical improvement for affected patients. A common procedure is vertebroplasty in which a bone substitute or bone cement (e.g., polymethylmethacrylate, hydroxylapatite compound or other material such as bone bits or bone filler of various types) is injected directly into the vertebral body. Kyphoplasty is a variation of a vertebroplasty which attempts to restore the height and angle of kyphosis of a fractured vertebra (of certain types), followed by its stabilization using injected bone cement. The procedure typically includes the use of a small balloon that is inflated in the vertebral body to restore the original vertebral body anatomy prior to cement delivery. When the catheter balloon is deflated, a cavitary void remains, which is then filled with materials similar to the vertebroplasty. While both procedures can have significant benefit for the patient, they are not without potential adverse effects. Once injected, bone cement is an inorganic material that acts as a foreign body, and thus, does not allow for complete healing, but may instead lead to bone disease. Additionally, bone cement is typically stiffer than bone, which may increase the incidence of adjacent level fractures in the spine. Also, bone cement leakage outside of the vertebral body may cause complications such as infection, bleeding, numbness, tingling, headache, and paralysis.

Thus, there remains a need for safe and effective kyphoplasty materials and procedures for treating collapsed or compressed vertebral bodies.

SUMMARY OF THE INVENTION

According to one aspect, a surgical balloon for expansion within a body cavity is provided. The balloon is composed of at least one umbilical cord vessel. In a preferred embodiment, the balloon is composed of at least one umbilical cord vein. According to one embodiment, the balloon further contains an effective amount of a demineralized bone matrix composition. According to one embodiment, the balloon further contains an effective amount of a human birth tissue material composition. According to one embodiment, the birth tissue material composition includes one or more of the components of the placental organ. According to one embodiment, the one or more of the components of the placental organ can include the placental globe, the umbilical cord, the umbilical cord blood, the chorionic membrane, the amniotic membrane, the amniotic fluid, and other gelatins, cells, and extracellular material of the placental organ.

According to one aspect, a method for stabilizing or treating a collapsed or compressed vertebral body of a patient is provided. The method includes the steps of introducing at least one balloon into the collapsed or compressed vertebral body and inflating the at least one balloon to create a void or space in the vertebral body. The balloon includes at least one umbilical cord vessel. According to one embodiment, the balloon contains an effective amount of a demineralized bone matrix composition. According to one embodiment, the balloon contains an effective amount of a human birth tissue material composition. According to one embodiment, the birth tissue material composition includes one or more of the components of the placental organ. According to one embodiment, the one or more of the components of the placental organ can include the placental globe, the umbilical cord, the umbilical cord blood, the chorionic membrane, the amniotic membrane, the amniotic fluid, and other gelatins, cells, and extracellular material of the placental organ. According to one aspect, the balloon remains in the body cavity post-surgery.

According to another aspect, a method of preparing a balloon for a surgical procedure is provided. The method includes the steps of recovering at least one umbilical cord vessel from a seronegative, healthy female via Cesarean section or vaginal delivery and sealing a first end of the umbilical cord vessel. According to one embodiment, the method further includes the step of adapting a second end of the umbilical cord vessel to engage a medical device capable of placing and inflating the balloon. According to one embodiment, the medical device is a cannula, mandrel, needle, or catheter.

According to another aspect, a kit comprising at least one surgical balloon and one inflation medium is provided. According to one embodiment, the inflation medium can include demineralized bone matrix composition, human birth tissue material composition, bone substitute, bone cement or a combination thereof. The kit may further comprise instructions for use.

BRIEF DESCRIPTION OF THE DRAWINGS

FIG. 1 illustrates a balloon according to one embodiment utilized in a kyphoplasty procedure.

DETAILED DESCRIPTION OF THE INVENTION

The present disclosure will now be described more fully hereinafter with reference to exemplary embodiments thereof. These exemplary embodiments are described so that this disclosure will be thorough and complete, and will fully convey the scope of the disclosure to those skilled in the art. Indeed, the present disclosure may be embodied in many different forms and should not be construed as limited to the embodiments set forth herein; rather, these embodiments are provided so that this disclosure will satisfy applicable legal requirements. As used in the specification, and in the appended claims, the singular forms "a", "an", "the", include plural referents unless the context clearly dictates otherwise.

As used herein, the term "umbilical cord vessel" refers to one of the vessels contained within the human umbilical cord, which is typically composed of two arteries and one vein. As used herein, the term "umbilical vein" refers to the single vein that passes through the human umbilical cord to the fetus and returns the oxygenated and nutrient blood from the placenta to the fetus.

As used herein, the term "effective amount" refers to an amount of a particular composition sufficient to elicit the desired therapeutic effects.

As used herein, the term "demineralized bone matrix" refers to an allograft bone product or derivative thereof that has had any inorganic mineral (e.g., calcium) substantially removed resulting in a matrix that includes a composite of non-collagenous proteins, growth factors, and collagen.

As used herein, the term "human birth tissue" includes, but is not limited to, elements of the placental organ such as, for example, the placental globe, the umbilical cord, the umbilical cord blood, the chorionic membrane, the amniotic membrane, the amniotic fluid, and other placental gelatins, fluids, cells and extracellular material obtained from a seronegative, healthy human. As used herein, the term "human birth tissue material composition" refers to an allograft product formulated from human birth tissue; the term can include, for example, placental organ biomolecules or placental material in suspension produced by morselization or disruption of the placental organ or components of the placental organ. As used herein, "morselization" means to grind up to particle form. Tissue morselization may occur by any art-recognized method of tissue disruption, including, but not limited to: milling, blending, sonicating, homogenizing, micronizing, pulverizing, macerating, or a combination thereof.

The present invention provides a surgical balloon adapted for various expansion procedures within a body cavity. The balloon is formed from at least one umbilical cord vessel. In one embodiment, the umbilical cord vessel is at least one human umbilical vein. Typically, the human umbilical cord contains two arteries and one vein, each of which is suitable for transplantation. Umbilical cord vessels are ideal for manufacture as biologic balloons because they: (i) lack branching; (ii) are generally of uniform cylindrical width; (iii) contain no one-way valves; and (iv) are elastic in nature.

In an alternate embodiment, the surgical balloon may be formed from at least one umbilical cord (outer membrane only) manufactured in substantially the same way as the umbilical cord vessel(s) as defined herein.

The umbilical cord vessel of the present invention is obtained from a human placenta having an attached umbilical cord following childbirth from a seronegative, healthy female. Potential human birth tissue donors providing informed consent are pre-screened during an examination of pre-natal medical records and blood test results. A comprehensive medical history and behavior risk assessment is obtained from the donor prior to donation, incorporating U.S. Public Health Service guidelines. Discussions with the physician(s) and/or the donor mother are conducted to identify circumstances that may lead to the exclusion of the donor or donated tissue. Additionally, a physical exam is performed on the donor to determine whether there is evidence of high risk behavior or infection and to determine the overall general health of the donor.

Infectious disease testing of donor blood specimens is performed for each tissue donor on a specimen collected at the time of donation or within seven days prior to or after donation. Advantageously, the methods that are used to screen for a communicable disease follow the regulations as set forth by the Federal Drug Administration and the American Association of Tissue Banks. Exemplary infectious disease testing includes, but is not limited to, antibodies to the human immunodeficiency virus, type 1 and type 2 (anti-HIV-1 and anti-HIV-2); nucleic acid test (NAT) for HIV-1; hepatitis B surface antigen (HBsAg); total antibodies to hepatitis B core antigen (anti-HBc—total, meaning IgG and IgM); antibodies to the hepatitis C virus (anti-HCV); NAT for HCV; antibodies to human T-lymphotropic virus type I and type II (anti-HTLV-I and anti-HTLV-II); and syphilis (a non-treponemal or treponemal-specific assay may be performed).

Human birth tissue is preferably recovered from a full-term Cesarean delivery of a newborn. Alternatively, human birth tissue is recovered from a full-term vaginal delivery of a newborn. After recovery, the human birth tissue is transported to a processing facility. The human birth tissue may be packaged with a sterile transport solution prior to transport. The sterile transport solution may include, but not be limited to, sterile water, sodium chloride in a concentration range from typically about 10% to typically about 20% by weight, Minimum Essential Medium, Dulbecco's Modified Eagle's Medium, Plasma Lyte-A, human albumin 25% solution, calcium-rich water, alkaline ionized water or acidic ionized water.

The subsequent steps of preparing the human birth tissue material are performed in a controlled environment (i.e., certified biological safety cabinet, hood or clean room). Instruments, solutions, and supplies coming into contact with the human birth tissue material during processing are sterile. All surfaces coming in contact with the human birth tissue material intended for transplant are either sterile or draped using aseptic technique.

The umbilical cord may be processed immediately, or may be stored in a sterile saline solution at a temperature between about 1° C. to about 10° C. prior to further processing. In one embodiment, the umbilical cord is separated from the placental globe as soon as possible after delivery of the newborn and is massaged to remove the umbilical cord blood. In an alternate embodiment, the umbilical cord blood is removed by identifying the ends of the arteries and vein and thoroughly irrigating the vessel(s) using smooth cannulation with a heparin solution (300 U/ml). The umbilical cord can be incised longitudinally using a scalpel and forceps, a grooved director, etc. Incising the cord longitudinally allows the cord to be laid flat, thereby allowing easy removal of the umbilical cord vessels using blunt and sharp dissection techniques. In an alternate embodiment, the umbilical cord vessels can be removed without longitudinally cutting the cord. For example, an umbilical cord vessel can be removed from the cord by grasping the vessel with forceps and gently pulling until the vessel is removed, thereby leaving the umbilical cord as an intact substantially tubular membrane. In an alternate example, the umbilical cord vessels may be removed with the aid of a cannulated coring instrument, thereby leaving the umbilical cord as an intact substantially tubular membrane. For example, during such a manual extraction procedure, a glass or stainless steel mandrel may be inserted into the lumen (e.g., vein lumen) to guide the manual dissection process. A standard scalpel and forceps can be used to remove connective tissue that surrounds the vessel.

In an alternative embodiment, the dissection of the vessels can be carried out via an automatized dissection procedure which minimizes damage to the vessels. For example, a stainless steel mandrel may be inserted into the vessel lumen to straighten the vessel and retain its tubular shape during excision. The umbilical cord may then be unwound and tensioned longitudinally. The mounted vessel may then be preserved.

When utilizing an automated cutting method, the umbilical cord can be further processed by securing the cord in a lathe upon removal from preservation. According to one embodiment, the rotational speed is then set to about 3,000 rpm. Using a cutting tool, the cord may be cut longitudinally. The cutting depth can be set to about 750 μm and the tool set to cut at a rate of about 5 mm/second.

The umbilical cord vessel(s) may be processed be any means know to those skilled in the art that preserves or enhances the biochemical and structural characteristics of the vessel(s). For example, an umbilical cord vein may be lyophilized, chemically preserved or cryopreserved prior to transplantation. Either before or after processing, the vessel (s) may be incised transversely, providing multiple "vessel segments". Each vessel segment will serve as the starting material for a surgical balloon. As such, multiple balloons may be manufactured from one umbilical cord vessel in a variety of sizes, depending upon the length of the vessel segments.

To form a surgical balloon, a first end of a vessel segment can be sealed by applying a tissue adhesive to form a unitary balloon structure with a sealed end and an open end. The open end of the resulting balloon is adapted to fit a medical device suited for placement of the balloon within a body cavity, e.g., a vertebral body. Suitable medical devices include, for example, a cannula, mandrel, needle, or catheter. The sealed end is formed via a variety of methods. According to one embodiment, a tissue adhesive is utilized. Tissue adhesives include, but are not limited to, fibrin glue, fibrinogen glue, a hydrogel tissue glue, cyanoacrylate and chondroitin sulfate aldehyde. In a preferred embodiment, the first end of the vessel segment is sealed by vacuum lamination. In an alternate embodiment, the first end of the vessel segment may be tied off with suture, e.g., 3-0 or 4-0 silk or Vicryl suture material. According to such an embodiment, the surgical balloon exhibits a suture holding capacity sufficient for the stabilization of a collapsed or compressed vertebral body of a patient. Suture holding capacity may be assessed by applying uniaxial stress to sections of the balloon. According to such a method, one end of the balloon is stitched with a single sterile 3-0 braided silk suture and the other end attached to an appropriate test rig. A stress (e.g., 0.005 N) is preloaded and data is recorded at an extension rate of 125 mm/min until failure. According to one embodiment, the balloon exhibits a failure rate at above 1.5 N. According to a preferred embodiment, the balloon exhibits a failure rate at above 2.5 N.

The resulting surgical balloon preferably exhibits a burst pressure high enough to aid in the stabilization of a collapsed or compressed vertebral body of a patient. Burst pressure is measured by progressive inflation of the vessel until rupture while simultaneously recording the change in vessel diameter. The ends of each vessel section are attached to stainless steel adapters and connected into a circuit of heavily walled silicone tubing. A modified syringe pump can then be attached to one end of the tubing with a pressure transducer attached to the distal end to monitor pressure change. The syringe pump injects distilled water into the circuit at a rate of about 5 ml/min until vessel rupture. Vessel diameter and pressure can be recorded over time using a video recording system. According to one embodiment, the surgical balloon exhibits a burst pressure of greater than about 500 mm Hg. According to a preferred embodiment, the surgical balloon exhibits a burst pressure of greater than about 1,000 mm Hg.

The balloon may be packaged and terminally sterilized using irradiation. In one embodiment, an electron beam irradiation is applied in an amount to about 45 kGy. The sterilized balloon may be stored for up to typically about two years from the date of processing. In one embodiment, the balloon may be stored under proper conditions for as much as five years following processing. The sterilized balloon may be stored in any container suitable for long-term storage. In one embodiment, the balloon is stored in a sterile double peel-pouch package.

The balloon may be inflated via hand injection with a syringe or other pressure source with a biocompatible fill material (inflation medium) such as a gas, liquid, gel or slurry, or fluid that becomes a resilient solid. In one embodiment, the inflation medium is bone cement, e.g., polymethylmethacylate ("PMMA"), or another biocompatible hardening substance which can flow into the balloon during initial delivery and then harden to become a rigid piece or semi-rigid piece or solid piece after placement inside a body cavity. The bone cement or other biocompatible hardening substance may conform to the shape of the cavity, i.e., it may conform to the shape of a space between bones and/or other joint structures, or another form chosen by the surgeon using tools and/or pressure to influence the final shape.

In a preferred embodiment, the inflation medium can include an effective amount of a demineralized bone matrix composition. The demineralized bone matrix composition may include a demineralized bone matrix in combination with at least one suitable carrier (e.g., glycerol, hyaluronic acid, gelatin, calcium sulfate powder), as well as other components to aid in osteoconductive support and the general healing cascade.

In a preferred embodiment, the inflation medium can include an effective amount of a human birth tissue material composition. The birth tissue material composition may include one or more of the components of the placental organ. Exemplary placental organ components include the placental globe, the umbilical cord, the umbilical cord blood, the chorionic membrane, the amniotic membrane, the amniotic fluid, and other placental gelatins, cells, and extracellular material and combinations thereof. The balloon can include a variety of placental organ components to aid in the healing cascade. In a preferred embodiment, the birth tissue material composition includes placental material in suspension produced by morselization or disruption of the placental organ or components of the placental organ.

In a preferred embodiment, the surgical balloon as described herein can be utilized to aid in stabilization of a collapsed or compressed vertebral body of a patient. The balloon is preferably utilized in surgical procedures such as, for example, kyphoplasty. Referring to FIG. 1, a medical professional can position a working medical device 102 (e.g., cannula, needle, a catheter or mandrel) through an incision (not shown) and through the pedicle 104 which guides the balloon 106 into a collapsed or compressed vertebral body 108. The balloon 106 can then be inflated as shown in FIG. 1, thereby stabilizing the fracture and restoring the natural vertebral body configuration, thus reducing deformity. According to an alternative embodiment, at least two balloons (not shown) as described herein are utilized. According to one embodiment, the surgical balloon can remain within the vertebral body post-surgery.

According to a preferred embodiment, the balloon contains an effective amount of a demineralized bone matrix composition to aid in stabilization of the vertebral body. According to another preferred embodiment, the balloon contains an effective amount of a human birth tissue material composition as described herein to aid in stabilization of the vertebral body, as well as aid in the healing cascade. The surgical balloon may also contain a combination of demineralized bone matrix composition and human birth tissue material composition, in addition to bone substitute and/or bone cement. Once in place and inflated, the open end of the balloon may be sealed by applying a tissue adhesive (e.g., cyanoacrylate), by suturing or by any other method known in the art.

In an alternate embodiment, the surgical balloon as described herein can be utilized in various medical procedures for gaining access to and/or maintaining an operating space within a cavity in a patient's body (e.g., balloon catheter), including, but not limited to, balloon angioplasty (e.g., peripheral angioplasty, coronary angioplasty, renal artery angioplasty, carotid angioplasty and cerebral arteries angioplasty), balloon septostomy via cardiac catheterization, balloon valvotomy, balloon sinuplasty, uterine balloon therapy or tuboplasty via uterine catheterization. The surgical balloon of the present invention may also be used in balloon expandable stents, gastric balloon surgery, balloon-filling defects or any medical procedure requiring balloon technology.

A kit for use by a medical professional is also provided. According to one embodiment, the kit includes one or more packaged surgical balloons as provided herein, in addition to an inflation medium, which is selected from the group consisting of demineralized bone matrix composition, human birth tissue material composition, bone substitute and bone cement. The kit may further include at least one set of instructions. The kit may further include a container adapted to accommodate and preserve the aforementioned components per applicable Food and Drug Administration guidelines.

Although specific embodiments of the present invention are herein illustrated and described in detail, the invention is not limited thereto. The above detailed descriptions are provided as exemplary of the present invention and should not be construed as constituting any limitation of the invention. Modifications will be obvious to those skilled in the art, and all modifications that do not depart from the spirit of the invention are intended to be included with the scope of the appended claims.

I claim:

1. A method of preparing a surgical balloon comprising:
   recovering at least one umbilical cord vessel from a seronegative, healthy female via Cesarean section or vaginal delivery; and
   sealing a first end of the umbilical cord vessel.

2. The method of claim 1, further comprising the step of adapting a second end of the umbilical cord vessel to engage a medical device capable of placing and inflating the balloon.

3. The method of claim 2, wherein the medical device is a cannula, mandrel, needle, or catheter.

4. The method of claim 2, further comprising the step of sterilizing the balloon via terminal sterilization.

* * * * *